United States Patent
Chen et al.

(10) Patent No.: US 10,456,430 B1
(45) Date of Patent: Oct. 29, 2019

(54) LACTOBACILLUS COMPOSITION FOR PREVENTION AND TREATMENT OF BACTERIAL VAGINOSIS

(71) Applicant: GenMont Biotech Incorporation, Tainan (TW)

(72) Inventors: Yi-Hsing Chen, Tainan (TW); Wan-Hua Tsai, Kaohsiung (TW); Wen-Ling Yeh, Tainan (TW)

(73) Assignee: Genmont Biotech Incorporation, Tainan (TW)

( * ) Notice: Subject to any disclaimer, the term of this patent is extended or adjusted under 35 U.S.C. 154(b) by 0 days.

(21) Appl. No.: 15/990,010

(22) Filed: May 25, 2018

(51) Int. Cl.
| | |
|---|---|
| *A61K 35/747* | (2015.01) |
| *A61P 31/04* | (2006.01) |
| *A61P 15/02* | (2006.01) |
| *A23L 33/135* | (2016.01) |

(52) U.S. Cl.
CPC .......... *A61K 35/747* (2013.01); *A23L 33/135* (2016.08); *A61P 15/02* (2018.01); *A61P 31/04* (2018.01); *A23V 2002/00* (2013.01); *A23Y 2220/67* (2013.01); *A23Y 2220/73* (2013.01)

(58) Field of Classification Search
CPC .... A23V 2200/3202; A23V 2200/3204; A23V 2002/00; A23L 33/135; A23L 33/195; A61K 9/1611; A61K 9/1647; A61K 35/747; A61K 9/1658; A61K 9/1652
See application file for complete search history.

(56) References Cited

U.S. PATENT DOCUMENTS

2016/0199424 A1* 7/2016 Berry ................... A61K 9/0031
424/93.3

FOREIGN PATENT DOCUMENTS

| CN | 105263504 A | 1/2016 |
|---|---|---|
| TW | I542353 B | 7/2016 |

OTHER PUBLICATIONS

Mastronnarino et al., (New Microbiol. 36, 229-238, 2013). (Year: 2013).*
P. Mastromarino et al., "Becterial vaginosis: a review on clinical trials with probiotics", New Microbiologica, 2013, pp. 229-238, vol. 36.
H. Tan et al., "Effects of metronidazole combined probiotics over metronidazole alone for the treatment of bacterial vaginosis: a meta-analysis of randomized clinical trials", Arch. Gynecol. Obstet., 2017, 9 pgs.
X. Ma et al., "Regulation of IL-10 and IL-12 production and function in macrophages and dendritic [version 1; referees: 3 approved]", F1000Research, 2015, 13 pgs.
(Continued)

*Primary Examiner* — Jana A Hines
(74) *Attorney, Agent, or Firm* — Muncy, Geissler, Olds & Lowe, P.C.

(57) ABSTRACT

A composition is used for prevention or treatment of bacterial vaginosis (BV) and regulation of vaginal immunity and said composition with effective amount is selected from the groups comprising *Lactobacillus rhamnosus* GMNL-680 and *Lactobacillus plantarum* GMNL-682; the composition of the present invention is used to prevent and treat bacterial vaginosis by inhibition of the growth of pathogens and regulation of the expression of immunoregulators and is prepared in the forms of pharmaceutical compositions, food or other combinations thereof.

9 Claims, 4 Drawing Sheets

(56) References Cited

OTHER PUBLICATIONS

D. V. Pechkovsky et al., "Different patters of cytokine regulation of phagocytosis and bacterial killing by human neutrophilis", International Journal of Antimicrobial Agents, 1996, pp. 33-40, vol. 7.
J. M. Macklaim et al., "Changes in vaginal microbiota following antimicrobial and probiotic therapy", Microbial Ecology in Health and Disease, 2015, pp. 1-8, vol. 26.
P. B. Heczko et al., "Supplementation of standard antibiotic therapy with oral probiotics for bacterial vaginosis and aerobic vaginitis: a randomised, double-blind, placebo-controlled trial", BMC Women's Health, 2015, pp. 1-12, vol. 15., No. 115.

\* cited by examiner

LACTOBACILLUS COMPOSITION FOR PREVENTION AND TREATMENT OF BACTERIAL VAGINOSIS

FIELD OF THE INVENTION

The present invention relates to a *Lactobacillus* composition containing *Lactobacillus*, and particularly to a *Lactobacillus* composition used for prevention and treatment of bacterial vaginosis and regulation of the immune function of the vagina.

BACKGROUND OF THE INVENTION

Bacterial vaginosis (BV) is the most common vaginitis and results from increased infection of non-single pathogenic bacteria (bad bacteria) that prefers basic environment due to elevated vaginal pH and is usually accompanied by a reduction of the normal *Lactobacillus* flora (probiotic) in the vagina. The common pathogens include *Gardnerella*, *Escherichia coli*, *Candida albicans*, *Candida tropicalis*, *Streptovecido vaginalis*, *Prevotella* and *Proteus* (Mastromarino P. et al., *New microbiologica*, 2013, 36, 229-238).

The infected women have the symptoms such as vaginal itching, vaginal odor, and abnotinal discharge. At present, two methods are available for diagnosis of BV: (1) Amsel criteria, identification of three out of the four following clinical symptoms will give a confirmed diagnosis: watery, gray, and white vaginal discharge attached to the vaginal wall; the vaginal pH is greater than 4.5; Whiff test: the discharge has a foul ammonia smell (foul-smelling fishy odor) in the presence of 10% KOH; the smear specimen shows a large number of bacteria adsorbed in the vaginal epithelial cells under the microscope and the cells are granular or clue cells with dotted appearance; (2) according to the Nugent score, a Gram stain scoring system for vaginal swab, a Nugent score ≥7 or 4-7 along with the presence of clue cells in the specimens will give a confirmed diagnosis of BV.

About the treatment for BV, the most common treatment is oral or topical administration of antibiotics, such as Metronidazole; however, use of antibiotics not only kills the pathogens of BV, but also leads to the death of the normal flora in the vagina. In addition, the growth of probiotic bacteria in the body is usually slower than pathogens and therefore medication usually will result in decreased immunity of patients which consequently changes the vaginal bacterial patterns in the patients and leads to repeated infections or even interferes with the treatment by generating drug-resistant pathogens. Moreover, there is also a potential risk of side effects of drugs. Despite the treatment of Metronidazole has significant clinical efficacy, there is still a relapse rate as high as 50% and the inevitable drawbacks of the antibiotics, and these are difficult problems that need to be addressed. Hence, searching for alternative drugs or treatments that have no side effects, higher efficacy and reduced recurrence is the major topic in the recent studies associated with BV (Hongying T. et al., *Archives of Gynecology and Obstetrics*, 2017, 295, 1331-1339).

In terms of indicators of treatments for BV, the aforementioned pathogens, changes of probiotics, and the inflammation, are associated with activation of the immune response and therefore the expression of the molecules relating to immune regulation is also a basis for reference, among which IL-10 and IL-12 are the immunoregulators that are produced in large amount upon invasion of pathogens and these two will co-express to promote immune defense and regulate immunologic homeostasis in a host (Ma X. et al., *F1000 Research*, 2015, 4 (F1000 Faculty Rev), 4, 1465). In addition to IL-10 and IL-12, Dmitry V. et al. also described the roles of IL-1β and IL-6 in bacterial infections in 1996 and these two are cytokines that promote inflammation. IL-1β promotes phagocytosis of bacteria by the immune cells in a host and IL-6 helps clearance of bacteria by neutrophils via a non-phagocytic way and regulates inflammation (Dmitry V. et al., Int. J. of Antimicrobial Agents, 1996, 1, p33-40). After administration of drugs, the reduced expression of IL-6 indicates alleviation of inflammation at the infected site, which means improvement in inflammation. Changes in the expression of the aforementioned cellular immunoregulators can be used as efficacy indicators for treating bacterial infection.

From the recent literatures, oral administration of probiotic (*Lactobacillus*) helps to restore the balance of normal flora in the vagina of the patients with BV after receiving the treatment of antibiotics. In the study published by Jean et al. in 2015, a new-generation drug for treating BV was proposed, Tinidazole, which can be used alone or in combination with *Lactobacillus reuteri* RC-14 and *Lactobacillus rhamnosus* GR-1 in patients, the probiotic bacterial flora of *Lactobacillus iners* and *Lactobacillus crispatus* in the vagina of patients showed a significant increase by detection of 16sRNA, a combination of antibiotics and probiotics is helpful for restoration of the floral patterns in the patient's vagina and prevention of the risk of recurrence (Jean M. et al., *Microbial Ecology in Health & Disease*, 2015; 14; 26: 27799). Likewise, in 2015, Piotr B. et al. indicated that the combination of antibiotics Metronidazole with prOVag® containing 3 probiotic strains (including *Lactobacillus gasseri* 57C, *Lactobacillus fermentum* 57A, and *Lactobacillus plantarum* 57B) can effectively extend the relapse time, reduce the vaginal pH and increase the number of *Lactobacillus* in the vagina of the patients with BV after receiving routine treatment of antibiotics.

Based on the aforementioned studies, the combined use of probiotics and antibiotics helps to prevent recurrence but the administration of antibiotics may still have problems, such as side effects, drug resistance, and high relapse rate. Therefore, some studies also tried to avoid the use of antibiotics and examined whether administration of probiotic composition alone can treat bacterial vaginosis. Related patents are briefly described as follows.

TW 1542353 discloses a food composition and/or pharmaceutical composition for treating vaginitis, comprising at least one *Lactobacillus* strain which is gastric acid, bile salt and Clotrimazole-resistant and is selected from the strains of *Lactobacillus acidophilus* F-1 and *Lactobacillus rhamnosus* CT-53 or the combination thereof, can inhibit expression of tumor necrosis factor-α (TNF-α) and interleukin-10(IL-10) and can further inhibit the symptoms of inflammation of the vaginal mucosa cells and can be orally administered or topically applied to the affected site. Nonetheless, said composition was primarily tested based on the direction of immunoregulation and the strains survived in the gastrointestinal tract were screened by bile salt, acid resistance and antifungal agents. However, the main cause of vaginitis is increased pathogens and reduced probiotic bacteria. The invention simply demonstrates its regulation of immunoregulators and alleviation of symptoms but fails to prove its effect on the flora in the vagina, provides no efficacy evaluation for the affected site in the patients and shows no evidence of reduction of the high relapse rate of vaginitis.

CN 105263504A reveals a bacterial composition for prevention and/or treatment of bacterial vaginosis, vaginitis and

*Escherichia coli* pathogens and/or *Gardnerella*-associated vaginal infections, said bacterial composition comprising LMGP-21021 (LP01) or LMG P-21020(LP02) and DSM26955 (LF15) or DSM26956 (LF16), said composition can inhibit the growth of *Escherichia coil* and *Gardnerella vaginalis* and induce the release of immunoregulators IL-4 and IL-10, said composition was prepared by combination of the bacteria strains and tara gum and was given to patients as vaginal tablets for clinical testing, the aforementioned tara gum plays the role of a physical barrier for pathogenic microorganisms. According to the results, 24 hours and 48 hours after administration of the tablets showed the highest inhibitory activity against *Gardnerella vaginalis* and was effective in blocking acute infections caused by *Gardnerella vaginalis*. The *Lactobacillus* composition of the present invention is combined with tara gum and administered as vaginal tablets. The composition can effectively reduce the Nugent scores of patients in the clinical trial, but the key feature of the present invention is that the tara gum can be applied to the affected site and form a physical barrier against pathogens to prevent acute infection. Therefore, the dosage form must be vaginal tablets or other routes that can be applied to the affected site directly. Because the affected site of the patients with vaginitis is relatively a hidden site, the vaginal tablets are not a convenient and fast route of administration. The affected site is rather fragile and inadvertent use may lead to secondary injury in the patients. Hence, how to treat vaginitis without the restrictions on dosage forms while reducing the recurrence rate is still a problem yet to be solved.

In light of the above, the inventor has successfully developed the composition comprising of the groups selected from *Lactobacillus rhamnosus* GMNL-680 and *Lactobacillus plantarum* GMNL-682 for prevention and treatment of bacterial vaginosis and regulation of immunity.

SUMMARY OF THE INVENTION

The present invention relates to a *Lactobacillus* composition for prevention and treatment of BV.

According to the invention, the *Lactobacillus* composition comprises *Lactobacillus rhamnosus* GMNL-680 and *Lactobacillus plantarum* GMNL-682, wherein said composition has the function of preventing or treating BV and regulation of immunity.

According to the invention, the aforementioned *Lactobacillus rhamnosus* GMNL-680 is deposited in Taiwan Food Industry Research and Development Institute with deposit number BCRC 910775 and in China Center for Type Culture Collection (CCTCC) with deposit number CCTCC M 2017766. *Lactobacillus plantarum* GMNL-682 is deposited in Taiwan Food Industry Research and Development Institute with deposit number BCRC 910776 and in China Center for Type Culture Collection (CCTCC) with deposit number CCTCC M 2017767.

According to the invention, the aforementioned composition is a pharmaceutical composition, nutritional supplement, health food or the combination thereof.

According to the invention, the composition may further comprise a pharmaceutically acceptable carrier.

According to the invention, the aforementioned composition is administered in the form of solutions, suspensions, emulsions, powders, troches, pills, syrups, buccal tablets, tablets, chewable gums, thick syrups, and capsules.

According to the invention, the aforementioned composition may further comprise edible materials, said edible materials include water, fluid dairy product, milk, concentrated milk, yogurt, sour milk, frozen yogurt, *Lactobacillus* fermented beverage, milk powder, ice cream, cheese, sold or semi-solid cheese, soy milk, fruit and vegetable juices, fruit juices, sports drinks, desserts, jellies, confectionery, baby foods, health foods, animal feeds, Chinese herbal medicines or dietary supplements.

According to the invention, the present invention provides a *Lactobacillus* composition used for the preparation of food or medicinal products that can prevent or treat bacterial vaginosis and regulate vaginal immunity, wherein the *Lactobacillus* composition comprises *Lactobacillus rhamnosus* GMNL-680 and *Lactobacillus plantarum* GMNL-682.

According to the invention, the aforementioned use for prevention and treatment of bacterial vaginosis refers to inhibition of the growth of pathogens that cause bacterial vaginosis.

According to the invention, the pathogens of the aforementioned bacterial vaginosis include *Escherichia coli* or *Gardnerella vaginalis*.

According to the invention, use of regulation of vaginal immunity is accomplished by regulation of the expression of immunoregulators.

According to the invention, the aforementioned immunoregulators refer to IL-1β and IL-6.

The first example of the present invention was proved by the Agar diffusion test and the composition comprises *Lactobacillus rhamnosus* GMNL-680 and *Lactobacillus plantarum* GMNL-682 and the composition of the combination of the two strains all can inhibit the growth of pathogens and showed a synergistic effect. In addition, said composition demonstrated better efficacy when compared with the published composition comprising *Lactobacillus rhamnosus* GR-1 and *Lactobacillus reuteri* RC-14.

The second example of the present invention also demonstrates cultivation of mouse splenocytes with *Lactobacillus rhamnosus* GMNL-680 and *Lactobacillus plantarum* GMNL-682 separately or together can enhance the expression of immunoregulators IL-10 and IL-12, achieving the effect of enhancement of vaginal immunity to further inhibit pathogens. In addition, said composition showed a better effect on stimulation of higher levels of immunoregulators expression when compared with the commercially available composition comprising *Lactobacillus rhamnosus* GR-1 and *Lactobacillus reuteri* RC-14.

The third example of the present invention also indicates that oral administration of GMNL-680 and GMNL-682 for one month significantly reduced the pathogen *Gardnerella vaginalis* by detecting the vaginal smear. The administration of GMNL-680 and GMNL-682 indeed improves the ability of vaginal flora and can effectively inhibit pathogens and reduce the expression of pro-inflammatory cytokines as well as occurrence of local immunity and actually improves the symptoms of patients with bacterial vaginosis.

The composition is safe and has no side effect. It can be used for alleviation of the symptoms of bacterial vaginosis and has no drawbacks of common antibiotics. In addition, said composition can achieve the effect of prevention or improvement of bacterial vaginosis by inhibition of vaginal pathogens and enhancement of host immunity.

DETAILED DESCRIPTION OF THE PREFERRED EMBODIMENTS

To fully understand the purpose, features and functions of the present invention, following examples are provided with embodiments to explain the details of the *Lactobacillus* composition of the present invention. However, it should be understood that the invention is not limited to the preferred embodiments shown. The materials used in the invention, unless specified otherwise, are commercially available materials. *Lactobacillus rhamnosus* GMNL-680 (hereinafter referred to as GMNL-680) is deposited in Taiwan Food Industry Research and Development Institute with deposit number BCRC 910775 and in China Center for Type Culture Collection (CCTCC) with deposit number CCTCC M 2017766. *Lactobacillus plantarum* GMNL-682 (hereinafter referred to as GMNL-682) is deposited in Taiwan Food Industry Research and Development Institute with deposit number BCRC 910776 and in China Center for Type Culture Collection (CCTCC) with deposit number CCTCC M 2017767.

Example 1: Inhibition of *Escherichia coli* and *Gardnerella vaginalis* by GMNL-680 and GMNL-682

The GMNL-680 and GMNL-682 strains used herein are the colonies of *Lactobacillus* obtained from healthy Taiwanese female adults which had been plated, screened and isolated and been characterized as *Lactobacillus rhamnosus* and *Lactobacillus plantarum*.

First, culture bacterial strains were prepared to be tested. The experimental colony was inoculated into 1 ml MRS (DeMan Rogosa-Sharpe) broth from the frozen vials of GMNL-680 and GMNL-682 and be incubated at 37° C. with oxygen for 20 hours and the number of colonies on the next day was estimated based on spectrophotometer readings at OD600 nm. For preparation of the colonies of pathogens, *Escherichia coli* was cultured in LB broth on a shaker at 37° C. for 16~18 hours and *Gardnerella vaginalis* was cultured in BHI (Brain Heart Infusion) broth (containing 5% defibrinated sheep blood) at 37° C. for 16-18 hours in the absence of oxygen, followed by determination of the number of colonies based on spectrophotometer readings at OD600 nm. The concentration of bacterial culture was adjusted to $5 \times 10^8$ cells/ml.

Continue to the next step, the agar diffusion test. The bacterial culture containing $5 \times 10^7$ CFU (colony forming unit) was evenly spread on the surface of the solidified agar medium in a Petri dish, an 11 mm glass tube was then used to create holes in the agar plates before adding 200 μl said bacterial culture into each hole, and the plates were incubated for different length of time based on the growth rate of each pathogen. After incubation for 24 hours and 48 hours, the results of inhibition zone were examined and an electronic digital caliper was used to measure the diameter of the zone of inhibition.

Figure 1A:
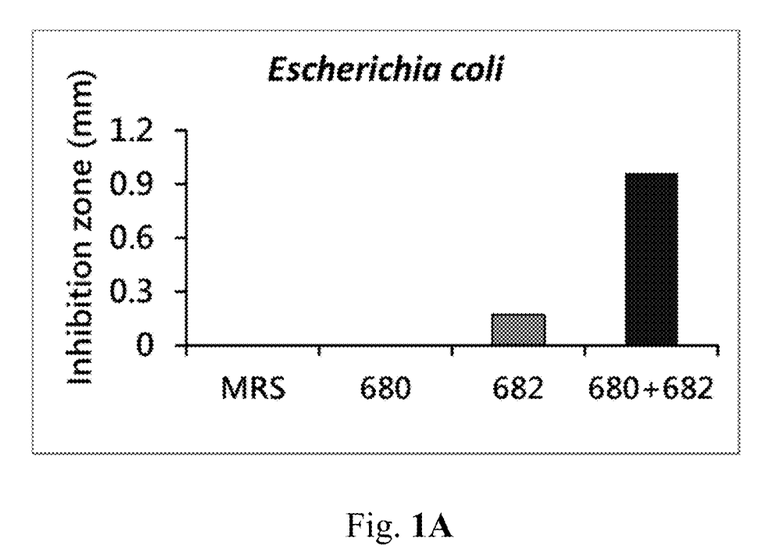
FIG. 1A shows the antimicrobial activity of *Lactobacillus rhamnosus* GMNL-680 and *Lactobacillus plantarum* GMNL-682 against *Escherichia coli*.
Figure 1B:
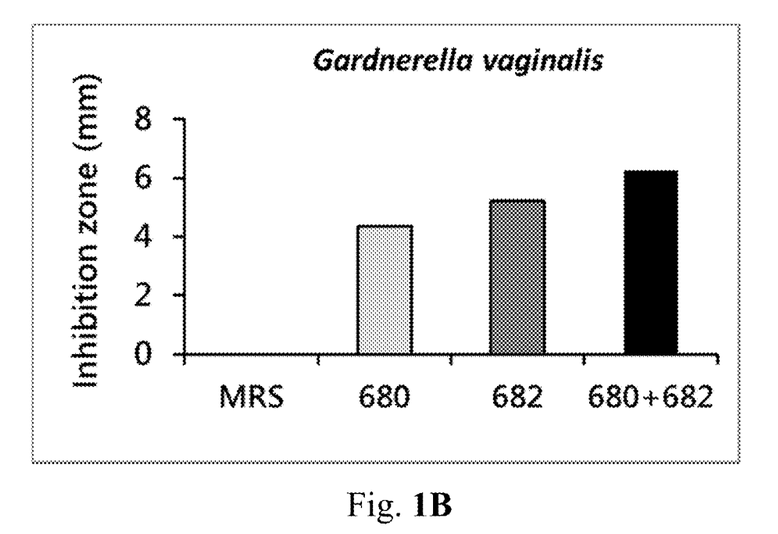
FIG. 1B shows the antimicrobial activity of *Lactobacillus rhamnosus* GMNL-680 and *Lactobacillus plantarum* GMNL-682 against *Gardnerella vaginalis*.

The experimental results indicated that GMNL-680 and GMNL-682 both had the inhibition zone against 2 strains of pathogens and the combination of the two strains showed a synergistic effect (FIG. 1A and FIG. 1B), indicating that the composition can inhibit bacterial growth.

Figure 2:
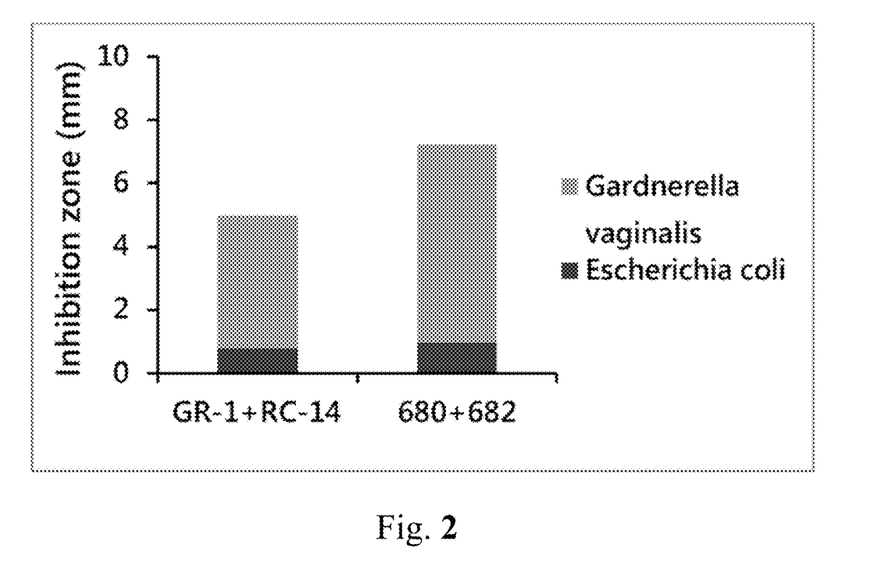
FIG. 2 shows the comparison of the antimicrobial activity between the *Lactobacillus* composition of the present invention and the disclosed *Lactobacillus* composition (*Lactobacillus rhamnosus* GR-1 and *Lactobacillus reuteri* RC-14).

In addition, this example further compared the inhibition zones of the other renowned strains of *Lactobacillus* for treating vaginitis (FIG. 2), composition of *Lactobacillus rhamnosus* GR-1 and *Lactobacillus reuteri* RC-14, and the composition of GMNL-680 and GMNL-682 disclosed in this invention had a better antimicrobial activity.

Example 2: GMNL-680 and GMNL-682 Regulate Local Vaginal Immunity Via Enhancement of the Expression of Immunoregulators IL-10 and IL-112

To test whether GMNL-680 and GMNL-682 can affect production of immunoregulators, in this example, the strains were co-cultured with the splenocytes of mice and the change of the expression levels of the immunoregulators (IL-10 and IL-12) in the supernatant was examined. First, cultivation of the bacterial strains is achieved. Preparation of the experimental bacterial strains was the same as described in Example 1. The experimental colony was inoculated into 1 ml MRS broth from the frozen vials of GMNL-680 and GMNL-682 before being incubated at 37° C. with oxygen for 20 hours; then, 10 μl overnight bacterial strains were inoculated into 1 ml MRS broth the next day before being incubated at 37° C. with oxygen for 20 hours; the number of colonies was estimated based on spectrophotometer readings at OD600 nm before replacing the MRS broth by RPMI1640 medium which contains 10% fetal bovine serum.

On the other hand, for separation of mouse splenocytes, 6-week-old BALB/c female mice were purchased from the National Laboratory Animal Center (NLAC) and housed in the animal room of GenMont Biotech Incorporation for 1 week before scarification by using $CO_2$. The spleen was removed and grounded before being suspended in RPMI1640 medium which contains 10% fetal bovine serum to make cell suspension cultures.

The mouse splenocytes in suspension were seeded into 96-well plates at the density of $4 \times 10^5$ cells per well and the experimental strains containing $4 \times 10^6$ CFU or $2 \times 10^7$ CFU (Multiplicity of infection, MOI=10 or 50) were added before being incubated at 37° C. with oxygen for 48 hours. The supernatant of co-culture was taken and analyzed by using Mouse IL-10, IL-12 ELISA kit (purchased from BD Biosciences) for quantification.

Figure 3A:
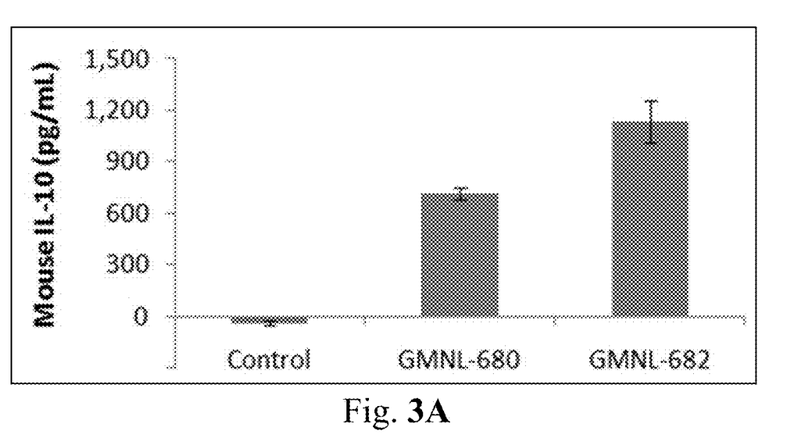
FIG. 3A shows the production of IL-10 by mouse splenocyte enhanced after co-culturing with *Lactobacillus rhamnosus* GMNL-680 and *Lactobacillus plantarum* GMNL-682.
Figure 3B:
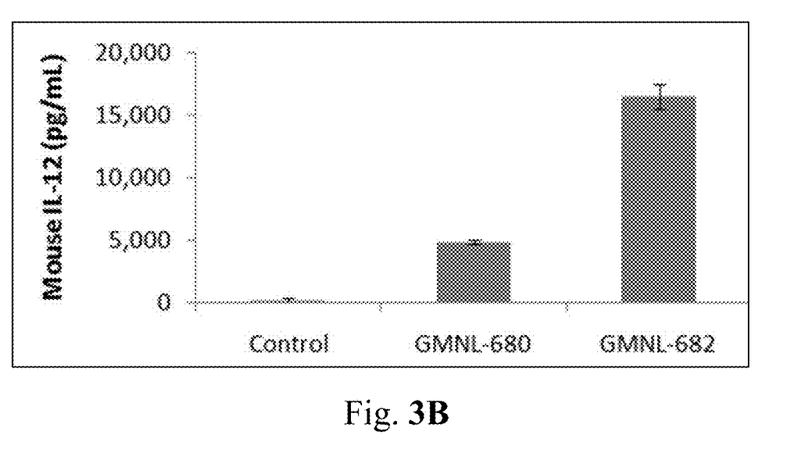
FIG. 3B shows the production of IL-12 enhanced by mouse splenocyte after co-culturing with *Lactobacillus rhamnosus* GMNL-680 and *Lactobacillus plantarum* GMNL-682.
Figure 4A:
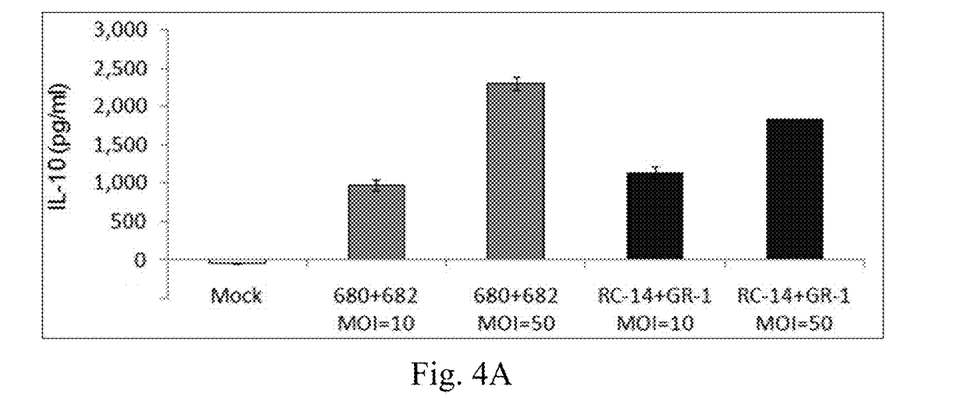
FIG. 4A shows the comparison of the enhanced production of IL-10 between the *Lactobacillus* composition of the present invention and the disclosed *Lactobacillus* composition (*Lactobacillus rhamnosus* GR-1 and *Lactobacillus reuteri* RC-14).
Figure 4B:
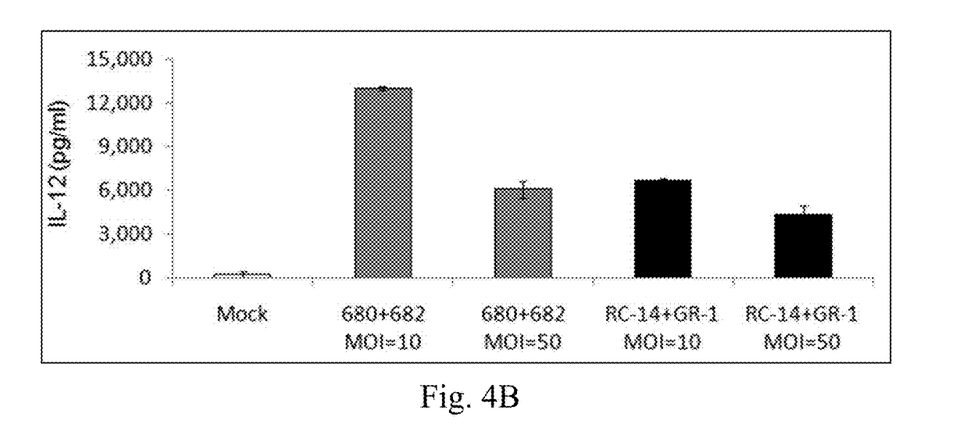
FIG. 4B shows the comparison of the enhanced production of IL-12 between the *Lactobacillus* composition of the present invention and the disclosed *Lactobacillus* composition (*Lactobacillus rhamnosus* GR-1 and *Lactobacillus reuteri* RC-14).

The results indicated that GMNL-680 or GMNL-682 (MOI=10) co-cultured with the mouse splenocytes significantly enhanced the expression of anti-inflammatory cytokines IL-10 and IL-12 (FIGS. 3A and 3B); in addition, the composition of GMNL-680 and GMNL-682 can stimulate mouse splenocytes to produce higher levels of IL-10 and IL-12 than the aforementioned renowned composition of RC-14 and GR-1.

Example 3: GMNL-680 and GMNL-682 can be Used for Treatments of Bacterial Vaginosis to Improve Local Discomfort To examine the clinical efficacy of the composition of the present invention, a clinical trial (Clinical Trial Registration Number: NCT03116789) was conducted. In this example, female patients with BV at the age of 53 years were given the composition of GMNL-680 and GMNL-682 (>1×10$^{10}$ CFU/day) daily for one month via oral administration to examine the effect of the composition on vaginitis. To determine the efficacy of the composition on BV, in addition to Nugent scoring system, vaginal smear was also collected for real-time quantitative polymerase chain reaction (Q-PCR) to detect the pathogen, *Gardnerella vaginalis*, and the change of the pro-inflammatory cytokines IL-1β and IL-6. Following are the methods of DNA and RNA extraction from vaginal specimens and quantitation of the expression by Q-PCR: First, DNA and RNA extraction from vaginal specimens: (1) For DNA extraction, a cotton swab was used for collection of vaginal specimen and the specimens were frozen in PBS for preservation before being thawed at the time of testing. The DNeasy Blood & Tissue Extraction Kit (Qiagen) was used for DNA extraction; (2) In addition, for RNA extraction, the vaginal specimen was precipitated by centrifugation before adding 1 ml TRIzol, followed by addition of 0.2 ml chloroform, the tube was flipped up and down 15 times and left at room temperature for 5 minutes to allow reaction; the supernatant was then collected and 0.5 ml isopropanol was added to the tube before being incubated at room temperature for 10 minutes, and the supernatant was removed after centrifugation, followed by washing and precipitation with 1 ml 75% alcohol, dried and suspended in 20-50 ul DEPC water for determination of RNA concentration; (3) Next, reverse transcription of RNA to produce cDNA was performed. First, the total volume of 1-5 ug extracted RNA was adjusted to 10 ul by RNase free water before adding 10× Random primer (2 ul) and 10 mM dNTP (1 ul), the sample was incubated at 65° C. for 5 minutes before being placed on ice for 2-3 minutes; next, 4 ul 5×RT (reverse transcription) buffer, 1 ul 0.1M DTT, 1 ul RNase inhibitor (Invitrogen, RNaseOUT™) and 1 ul RT enzyme (Invitrogen, SuperScript® III) were added in the sequential order and mixed at room temperature for 5 minutes before incubation at 50° C. for 60 minutes and at 70° C. for 15 minutes to complete reverse transcription.

Continue to Q-PCR for quantitation of the expression. The extracted DNA or cDNA obtained by reverse transcription was diluted in sterile water and 2 μl was taken and mixed with 2× Rotor-Gene SYBR Green PCR Master Mix (Qiagen, Cat. 204076) for Q-PCR; the result is represented as $2^{-\Delta CT}$ ($2^{-\Delta CT=2-(CT\ target\ gene-CT\ GAPDH)}$ or $2^{-(CT\ GV-CT\ total\ bacterial)}$), wherein Δ is the relative expression level which is obtained by deduction of its GAPDH or total bacterial. The higher the value the higher the expression level and the results are shown in Table 1. Female patients with BV at 53 years of age were given the composition of GMNL-680 and GMNL-682 (>1×10$^{10}$ CFU/day) daily for one month via oral administration and the Nugent score for detection of BV decreased significantly and the expression levels of the vaginal pathogen, *Gardnerella vaginalis*, and the pro-inflammatory cytokines IL-1β and IL-6 also showed significant decreases, suggesting this composition indeed can effectively inhibit vaginal pathogens and reduce induction of local immune response in female vagina and is capable of improving the discomfort and severity of vaginitis.

TABLE 1

|  | Before | After |
|---|---|---|
| Nugent Score | 5 | 3 |
| *Gardnerella vaginalis*/total bacterial ($2^{-\Delta CT}$) | 0.57236 | 0.00053 |
| IL-1β/GAPDH ($2^{-\Delta CT}$) | 2.0705 | 0.3711 |
| IL-6/GAPDH ($2^{-\Delta CT}$) | 0.0009698 | 0.0000317 |

The present invention proves that the compositions of GMNL-680 or GMNL-682 and the composition of two bacterial strains can inhibit overgrowth of the vaginal pathogens and the composition of two strains have a synergistic effect. In addition, separate cultures of mouse splenocytes with GMNL-680 or GMNL-682 can both stimulate the splenocytes to release cytokines and enhance the expression of IL-10 and IL-12 to achieve the effect of immunoregulation. Moreover, regardless of inhibition of pathogens or enhancement of the release of immunoregulators, the composition has better efficacy when compared with the published composition containing *Lactobacillus rhamnosus* GR-1 and *Lactobacillus reuteri* RC-14. Also, according to the clinical trial, after administration of the composition of the present invention for one month, the Nugent score of the affected site of the patients with BV showed a remarkably decrease and the expression of *Gardnerella vaginalis* and pro-inflammatory cytokines IL-1β and IL-6 were also decreased significantly, indicating that administration of GMNL-680 and 682 can indeed be used for treatment of bacterial vaginosis and regulation of vaginal immunoregulators and consequently for treatment of vaginitis and alleviation of discomfort.

The *Lactobacillus* composition is a safe composition of *Lactobacillus rhamnosus* GMNL-680 and *Lactobacillus plantarum* GMNL-682 and has no side effect. It can regulate the expression of immunoregulators to enhance vaginal immunity and consequently alleviate the symptoms of bacterial vaginosis. In addition, this composition has better efficacy when compared with the published *Lactobacillus* composition and does not need to concern which the normal flora is killed or the floral pattern in the vagina is changed after treatment of antibiotics and thus eliminates the worries about recurrence of infection as well as the risks of potential drug-resistance and side effects of drugs. The present invention can achieve the effect of prevention or improvement of bacterial vaginosis by inhibition of vaginal pathogens and enhancement of the local vaginal immunity of the host.

What is claimed is:

1. A method for treating bacterial vaginosis and regulating vaginal immunity comprising: administering to a subject a composition comprising an effective amount of *Lactobacillus rhamnosus* GMNL-680 with the deposition number CCTCC M 2017766 and *Lactobacillus plantarum* GMNL-682 with the deposition number CCTCC M 2017767; wherein the effective amount is at least 10$^{10}$ CFU per day.

2. The method as recited in claim 1, wherein the preventing or treating bacterial vaginosis refers to inhibition of the growth of pathogens that cause bacterial vaginosis.

3. The method as recited in claim 2, wherein the pathogens that cause bacterial vaginosis refer to *Escherichia coli* or *Gardnerella vaginalis*.

4. The method as recited in claim 1, wherein the regulating of vaginal immunity is accomplished by regulating the expression of immunoregulators.

5. The method as recited in claim 4, wherein the immunoregulators include IL-1β and IL-6.

6. The method as recited in claim 1, wherein the composition is a pharmaceutical composition, nutritional supplement, health food or combinations thereof.

7. The method as recited in claim 6 wherein the composition further comprises a pharmaceutically acceptable carrier.

8. The method as recited in claim 6, wherein the composition is administered in the form of solutions, suspensions, emulsions, powders, troches, pills, syrups, buccal tablets, tablets, chewable gums, thick syrups, capsules, pessaries or topical preparations.

9. The method as recited in claim 6, wherein the composition further comprises edible materials, wherein said edible materials include water, fluid dairy product, milk, concentrated milk, yogurt, sour milk, frozen yogurt, *Lactobacillus* fermented beverage, milk powder, ice cream, cheese, sold or semi-solid cheese, soy milk, fruit and vegetable juices, fruit juices, sports drinks, desserts, jellies, confectionery, baby foods, health foods, animal feeds, Chinese herbal medicines or dietary supplements.

\* \* \* \* \*